US00PP10828P

United States Patent [19]

Tucker

[11] Patent Number: Plant 10,828

[45] Date of Patent: Mar. 16, 1999

[54] MINIATURE ROSE PLANT NAMED 'TUCKACH'

[76] Inventor: Robert T. Tucker, 9404 Hunting Hills Dr., Franklin, Tenn. 37607

[21] Appl. No.: 969,306

[22] Filed: Nov. 13, 1997

[51] Int. Cl.[6] ..... A01H 5/00

[52] U.S. Cl. ..... Plt./8.1

[58] Field of Search ..... Plt./8.1, 23

*Primary Examiner*—Howard J. Locker

[57] ABSTRACT

This invention relates to a new and distinct variety of miniature rose plant primarily identified by its white buds and flowers, hybrid tea form and semi-glossy green foliage.

1 Drawing Sheet

The present invention relates to a new and distinct variety of hardy, dwarf, bush type rose plant of the miniature class; the variety being primarily characterized — as to novelty — by buds and flowers of a uniform white color which generally are of exhibition (Hybrid Tea) form.

The variety is further characterized by: An abundance of bloom, with flowers often borne singly and also several to the stem in loose clusters. No fragrance. A plant which is vigorous, tall, upright shape with medium growth habit and semi-glossy foliage. The plant, which has an above average height of 18–36 inches, can easily be maintained at lesser height by occasional trimming. A plant which grows and blooms satisfactorily both in the greenhouse and outdoors; is good for growing in pots; and provides excellent garden decoration as well as cut flowers. The present variety of miniature rose was originated by me in my hybridizing garden located at Franklin, Tenn. under conditions of careful control and observation, as a cross between an unnamed seedling of 'Little Darling' (U.S. Plant Pat. No. 1,581) X 'Yellow Magic' (not patented) as the seed parent and an unnamed seedling of 'Rise n' Shine' (U.S. Plant Pat. No. 4,231) X Laguna (not patented) as the pollen plant.

Subsequent to origination of the variety, I successfuly asexually reproduced it at my hybridizing garden, located as aforesaid, by cuttings; the reproduction having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The Royal Horticultural Society Colour Chart, except where common terms of color definition are employed.

Class: Miniature.

*Variety identification.*—TUCkach (Commercial synonym: Cachet).

Flower

Observations made from specimens grown in a garden environment at Franklin, Tenn. in May 1995 through September 1997.

Blooming habit: Continuous.

Bud:

*Size.*—¾ to 1 inch long when the petals start to unfurl.

*Form.*—The bud form is long and tapered.

*Color.*—When the sepals first divide, bud color is light green to white.

*Sepals.*—Color: Light to medium green. Surface texture: Mostly smooth.

*Peduncle.*—Length: Short to Medium. ½ to 1inch. Surface: Tiny "hairlike" prickles. Strength: Stiff. Color: Light green.

Bloom:

*Size.*—Medium to Large for a dwarf-type rose; Average open size is 2.0 inches.

*Borne.*—Singly and sometimes in loose clusters of 2 to 4 flowers.

*Stems.*—Small and strong. Average flowering stem length is typically 8 to 10 inches, occasionally up to 16 inches.

*Form.*—High centered; Reflexed petals; Exhibition; When fully open stamens show.

*Petalage.*—Double; Number of petals under normal conditions: 25–30. Arranged regularly plus some small petaloids. Petals have excellent substance.

*Color.*—The petals' upper and lower side is White R.H.S. 155D. At first opening, blooms may have a slight hue of green (Yellow-Green Group-145D).

*Variegations.*—None.

*Discoloration.*—The general tonality at the end of the first day: No change. At the end of the third day: No Change.

*Fragrance.*—Slight to none.

*Lastingness.*—On plant, up to 7 days on average.

Reproductive parts:

*Anthers.*—Size: Medium; Quantity: Many; Color: Yellow; Arrangement: Regular around styles.

*Filaments.*—Varying length, short to medium long, yellow.

*Pollen.*—Quantity: Very Slight; Color: Golden yellow.

*Styles.*—Color: reddish.

*Stigmas.*—Color: whitish.

*Ovaries.*—All enclosed in calyx.

*Hips.*—Female reproductive system appears to be sterile.

*Seeds.*—Has not demonstrated the ability to produce seeds.

Growth:

*Habit.*—Dwarf; mostly upright; vigorous to 3 feet.

Foliage:

*Leaflets.*—Number on normal mid-stem leaves: 5 or 7.

*Size.*—Medium; Leaflets vary in length from ½ to 2 inches.

*Quantity.*—Abundant.

*Color.*—New foliage: Lower and upper surface; Green Group 137A.

*Old foliage.*—Upper surface: Green Group 136B. Lower surface: Green Group 139C.

Leaflets:

*Shape.*—Pointed oval.

*Texture.*—Smooth; semi-glossy.

*Edge.*—Serrated.

*Serration.*—Single, small.

*Petiole rachis.*—Smooth and light green. Some reddish coloration on new growth.

*Petiole Underside.*—May have several prickles.

*Stipules.*—Medium to short length (¼ to ½ inch).

Wood:

*New wood.*—Color: Reddish but turns light green very quickly. Bark smooth.

*Old wood.*—Color: Green; Bark smooth.

Prickles:

*Quantity.*—Moderate.

*Form.*—Varying sizes from small prickles to medium thorns; Medium thorn size (⅜ to ½ inch); Prickles project straight from stem.

The miniature rose plant and its flowers as herein described may vary in slight detail due to climatic, soil and cultural conditions under which the variety may be grown; the present description being of the variety as grown at Franklin, Tenn.

The following is claimed:

1. A new and distinct variety of miniature rose plant of hardy, dwarf, upright habit, substantially as illustrated and described, characterized by buds and flowers of exhibition form, essentially white in color, with reverse same (white), and further characterized by a plant of upright shape, vigorous, with the main stems and shoots being moderately thorny, the said plant being easy to propagate from cuttings, with an abundance of flowers borne singly or several to a stem.

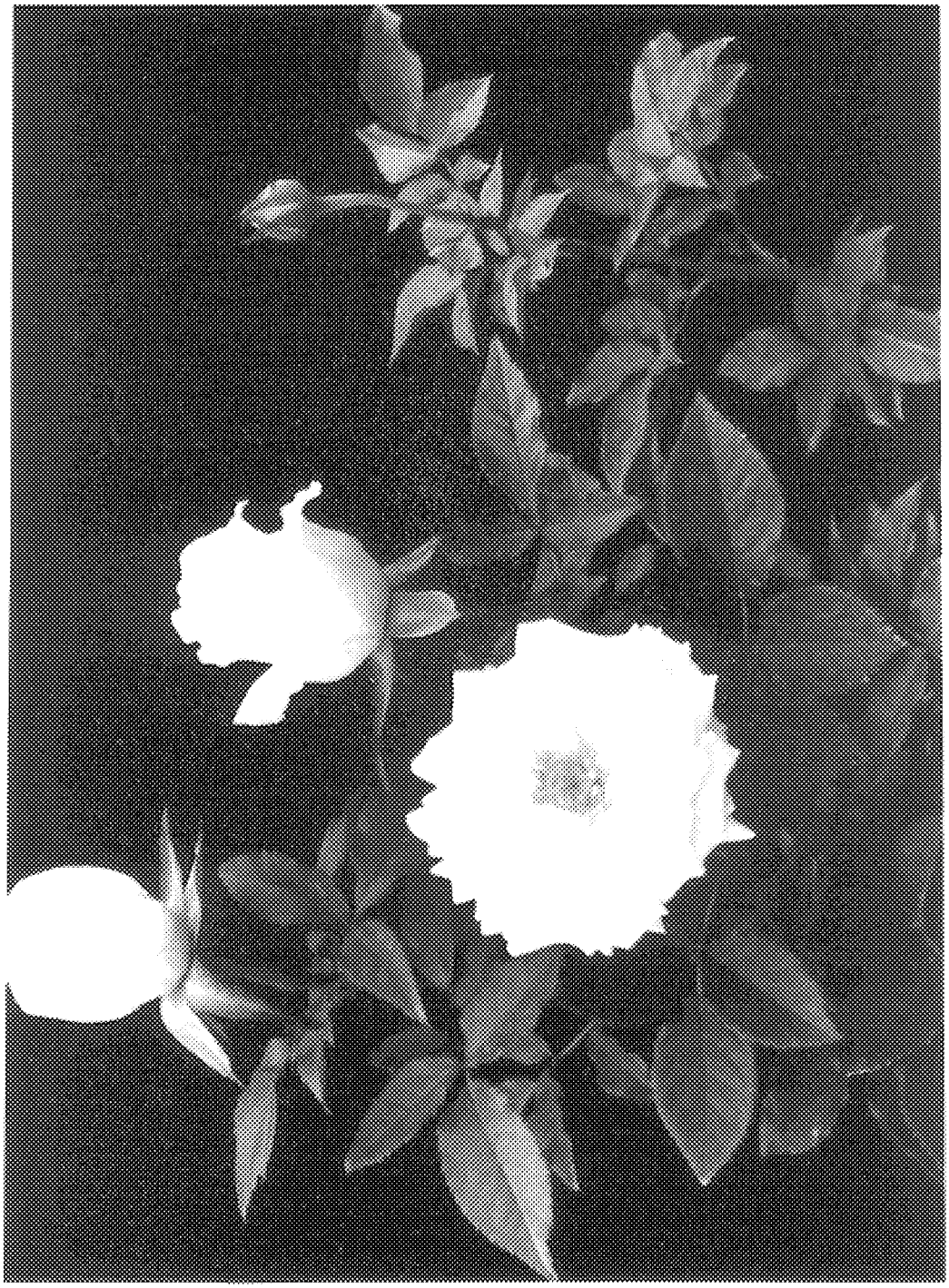

* * * * *